United States Patent [19]

Verweij et al.

[11] Patent Number: 5,109,132
[45] Date of Patent: Apr. 28, 1992

[54] PROCESS FOR THE PREPARATION OF 3-EXOMETHYLENE CEPHAM DERIVATIVES

[75] Inventors: Jan Verweij, Leiden; Jan J. De Koning, Rijswijk; Hendrik A. Witkamp, Pijnacker, all of Netherlands

[73] Assignee: Gist-Brocades N.V., Netherlands

[21] Appl. No.: 581,518

[22] Filed: Sep. 10, 1990

Related U.S. Application Data

[62] Division of Ser. No. 337,525, Feb. 15, 1989, Pat. No. 4,985,554.

[30] Foreign Application Priority Data

Jul. 13, 1987 [EP] European Pat. Off. ........ 87-201323.0

[51] Int. Cl.$^5$ ............................................ C07D 501/04
[52] U.S. Cl. .................................... 540/230; 540/215; 540/219
[58] Field of Search .................... 540/215, 230, 219

[56] References Cited

U.S. PATENT DOCUMENTS 4,354,022 10/1982 Takaya et al. ..................... 544/28

OTHER PUBLICATIONS

Kaiser et al, J. Org. Chem Vol. 35 pp. 2430-2433 (1978).
Brenner et al, J. Chem. Soc. Perkins Trans I pp. 1265-1272 (1991).

Primary Examiner—Nicholas S. Rizzo
Attorney, Agent, or Firm—Bierman and Muserlian

[57] ABSTRACT

A process is provided for the preparation of 3-methylene and 3-halomethylene cepham derivatives via 3-phosphoniomethyl-3-cephem derivatives, which in turn can be prepared from 3-halomethyl-3-cephem derivatives. The preparation can be carried out with or without isolating the intermediate phosphonium cepham compounds. The 3-methylene and 3-halomethylene cepham derivatives and in particular the 1-oxo and 1,1-dioxo cepham compounds are also prepared by reducing a 3-halomethyl-3-cephem derivative with activated metal, preferably zinc or magnesium.

4 Claims, No Drawings

PROCESS FOR THE PREPARATION OF 3-EXOMETHYLENE CEPHAM DERIVATIVES

PRIOR APPLICATION

This application is a division of U.S. patent application Ser. No. 337,525 filed Feb. 15, 1989, now U.S. Pat. No. 4,985,554.

The invention relates to a new process for the preparation of 3-exomethylene cepham compounds (also referred to hereinafter as 3-methylene cepham compounds) are valuable intermediates in the semi-synthetic preparation of various therapeutically useful antibiotics. For example, 3-methylene cepham sulfoxides (also named: 3-methylene-1-oxocepham compounds) can be converted into 7-ADCA had derivatives thereof, into 7-ACA and other 3-acyloxymethyl cephalosporins, and into 3-heteroarylthiomethyl cephalosporins. Some of these compounds can be used as such in pharmaceutical preparations, others have to be converted further before they are suitable for therapeutic use.

Several routes have been known so far to produce 3-methylene cepham compounds, but these routes are almost entirely limited to the preparation of 3-methylene cepham sulfides.

U.S. Pat. No. 4,354,022 discloses a process for preparing 3-methylene cepham sulfides by reacting inter alia 3halomethyl-3-cephem sulfides with a combination of a metal (zinc, tin or iron) and certain ammonium salts (ammonium halides, ammonium carbonate and ammonium acetate). It is noted that of the 3-halomethyl-3-cephem compounds only chloromethyl is exemplified in this reference.

In Chem. Pharm. Bull. 36(2) 528–591 (1988) the preparation of 7-amino-3-methylenecepham-4-carboxylic acid is described, by reduction of the corresponding 3-(5-methyl-1,3,4-thiadiazol-2-yl)thiomethyl-3-cephem compound with zinc either in aqueous acidic or in anhydrous neutral medium.

Other known methods for the preparation of 3-methylene cepham sulfides include the conversion of 3-acetoxymethyl, 3-thiomethyl and 3-carbomoyloxy cepham sulfides.

In Synth. Comm. 16(6) 649–652 (1986) the preparation of 3-methylene-1-oxocepham compounds is described, by reduction of the corresponding 3-acetoxymethyl cephem compounds with activated zinc dust and ammonium chloride.

The present invention now provides a new process for the preparation of 3-methylene and 3-halomethylene cepham compounds of high purity and in good yields.

It has now surprisingly been found that such 3-methylene cepham compounds can be advantageously obtained from the corresponding 3-phosphoniomethyl-3-cepham compounds can be advantageously obtained from the corresponding 3-phosphoniomethyl-3-cephem compounds. Therefore, according to one aspect of the invention there is provided a process for the preparation of 3-metylene or 3-halomethylene cephem derivatives of the general formula 1:

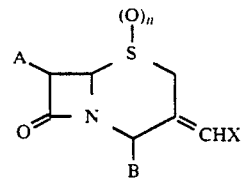

wherein
A is an amino group or a protected amino group,
B is a carboxy group or a protected carboxy group, or a salt thereof,
X is hydrogen or halogen, and
n is 0, 1 or 2,
which comprises converging a 3-phosphoniomethyl-3-cephem derivative of formula 2:

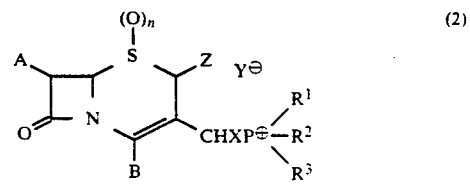

wherein
A, B, X and n are each as defined above,
Y is halogen,
Z is Y or hydrogen, and
$R_1$, $R_2$ and $R_3$ represent the same or different alkyl, aryl or aralkyl groups,
into a compound of formula 1.

Suitable "protected amino groups" as used in this specification include amino groups substituted with a suitable protective group which are conventionally used in cephalosporin and penicillin chemistry as protective groups at position 7 and position 6, respectively, acylamino, phenyl(lower)alkylamino, (cyclo)alkylamino, (cyclo)alkylideneamino, and the like.

Suitable "acylamino" groups include aliphatic, aromatic and heterocyclic acylamino groups, the acyl group being for example formyl, acetyl, propionyl, butyryl, valeryl, hexanoyl, methoxycarbonyl, ethoxycarbonyl, t-butoxycarbonyl, benzoyl, toluyl, phenylacetyl, phenylpropionyl, phenoxy carbonyl, etc. etc. Basically, the same groups as mentioned in U.S. Pat. No. 4,354,022, herein incorporated by reference, and other groups known to persons skilled in the art of cephalosporin and penicillin chemistry are included within the scope of this invention.

Suitable "protected carboxy groups" as used in this specification include carboxy groups substituted with a suitable protective group, which are conventionally used in cephalosporin and penicillin chemistry as carboxy-protective groups at position 4 and position 3, respectively.

Suitable examples of such protected carboxy groups include esters, such as the methyl ester, ethyl ester, propyl ester, butyl ester, in particular the t-butyl ester, benzyl ester, optionally substituted, such as the 4-nitrobenzyl ester, diphenylmethyl ester, etc. etc. See also U.S. Pat. No. 4,354,022, referred to above.

Suitable "salts" of the compounds of formula 1, and the starting compounds (and intermediates) for preparing these compounds, include conventional non-toxic salts, such as those listed in U.S. Pat. No. 4,354,022, referred to above.

Preferred compounds of formula 1 which can be made by the method according to the present invention are 3-methylene cepham derivatives, and especially the 3-methylene 1-oxocepham (most preferred) and 3-methylene 1,1-dioxocepham compounds.

The reaction defined above is suitable carried out by adding a previously prepared suspension or solution of an inorganic salt in water which is adjusted to a pH above 7, to the phosphonium salt of formula 2.

Suitable inorganic salts include tin salts, such as stannous or stannic halides; stannites, e.g. sodium stannite; sodium, potassium, aluminium, boron, phosphorus, zinc and tellurium salts, especially halides; and combination thereof. Of these, stannous chloride and bromide, and stannites are preferred, stannous chloride being most preferred.

The organic salt is preferably suspended or dissolved in a little water. The pH is then preferably adjusted to values of 9 and higher by adding a strong hydroxide solution. The suspension or solution is then added to the phosphonium cephem compound, which is preferably in solution. Suitable solvents are, for example, tetrahydrofuran (preferred), methylene chloride and acetonitrile. The reaction takes also place when adding a strong base without an inorganic salt.

The reaction conditions are not very critical and may be optimized experimentally. Suitable temperatures are usually in the range of between 0° C. and the boiling point of the reaction mixture, and preferably at about 40° C. The reaction time may vary widely, but is suitably in the range of between some minutes and several hours, usually between 1-2 hours. Isolation and purification is suitable carried out by usual techniques, for example by adjusting the pH to neutral, pouring out the reaction mixture in an organic solvent which is poorly miscible with water, extracting, separating, washing, evaporating, redissolving, etc.

The conversion of the phosphonium salt into the exomethylene group in the presence of a base was surprising because the formation of a phosphorane group was expected.

The phosphonium cephem compounds (sulfides, sulfoxides and sulfones) of formula 2 are believed to be novel and form an aspect of the invention. These compounds can be conveniently prepared by reacting a corresponding (2-halo)-3-halomethyl-3-cephem compound of the general formula 3:

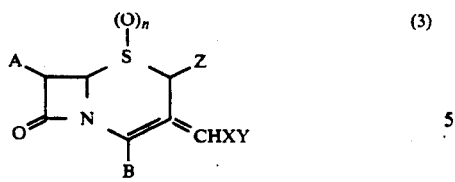
(3)

wherein
A, B, X, Y, Z and n are each as defined above, with a phosphine compound in a suitable solvent. Suitable phosphines are, inter alia, trialkyl ($C_{1-6}$, straight or branched), triaryl or triaralkyl (both unsubstituted or substituted by one or more groups) phosphines, of which triphenyl phosphine is preferred. Preferably, the carboxy group at position 4 is protected by a suitable protecting group. Suitable solvents include tetrahydrofuran, which is preferred. Although the reaction conditions are not very critical the reaction is conveniently carried out at slightly elevated temperature (about 40°C.) for several hours (usually about 3 hours) in an inert atmosphere.

The desired phosphonium cephem compounds may also be prepared from other phosphonium cephem compounds, by converting one or more groups of the molecule. For example, a 3-phosphoniomethyl-3-cephem sulfide derivative can be prepared from the corresponding 3-phosphoniomethyl-3-cephem sulfoxide derivative, for example by reacting the sulfoxide with $PCl_3$.

Isolation and purification of the resulting phosphonium cephem compounds may be carried out by usual techniques (e.g. centrifugation, washing and drying).

Preferred phosphonium cephem compounds are such compounds of formula 2 in which X and Z are hydrogen and Y is bromine. Most preferred are those compounds in which, moreover, n is 1 and $R_1$, $R_2$ and $R_3$ are phenyl.

The starting (2-halo)-3-halomethyl-3-cephem derivatives (sulfides, sulfoxides and sulfones) are either known compounds or may be prepared by methods known for the preparation of analogous compounds. See, for example, EP-A-0 015 629 and EP-A-0 034 394. Preferably, 3-bromomethyl-3-cephem derivatives are used as starting compounds. Such 3-bromomethyl- 3cephem derivatives are suitable prepared, for example, by bromination of the corresponding 3-methyl-3-cephem compounds.

The bromination is suitably carried out with N-bromosuccinimide (NBS) in a non-hydrolytic solvent, for example methylene chloride or methylene chloride/acetic acid, preferably using an initiator and most preferably light (irradiation). Preferably, the bromination reaction with NBS and light is carried out at low temperature (about 0° C.), usually for a time between some minutes and several hours, for example between about 1 and 4 hours. If desired, by-products which may be formed during the bromination reaction, such as 2-bromo-3-bromomethyl-3-cepham derivatives may be debrominated at the 2-position by the addition of a suitable debrominating agent, for example a phosphite, such as tributyl phosphite. After the bromination the reaction mixture is isolated and purified according to usual techniques to give the desired 3-bromo-3-cepham compounds.

Similar techniques can be applied for the preparation of other (2-halo)-3-halo-3-cephem compounds, which are all within the skill of the average expert.

According to another preferred embodiment of the invention the 3-methylene and 3-halomethylene compounds of formula 3 can also be directly prepared from the 3-halomethyl-3-cephem derivatives of formula 3 via the intermediate phosphonium cephem compounds of formula 2, but without isolating said intermediates. The reaction conditions are substantially identical to the conditions described above for the separate preparation of the compounds of formula 1 from the 3-phosphoniomethyl-3-cephem derivatives of formula 2 and the preparation of the latter compounds from the 3-halomethyl-3-cephem derivatives, respectively.

According to a further preferred embodiment of the invention the 3-methylene and 3-halomethylene derivatives of formula 1, and especially those in which n is 1 or 2, can be prepared in good quality and high yield by reducing the (2-halo)-3-halomethyl-3-cephem derivatives of formula 3 with activated metal, for example zinc or magnesium, and preferably activated zinc, in the presence of an ammonium salt or an amine. The yields obtained with this process were found to be substantially higher than the yields reported by McShane and Dunigan in Synth. Comm. 16(6) 649–652 (1986), referred to above.

The reaction is preferably carried out by adding the activated metal powder to a 3-halomethyl, preferably a 3-bromomethyl-3-cepham derivative, to which previously a solution of an ammonium salt in water was added. If desired, the cephem derivative is dissolved in a suitable solvent, such as acetone or dimethylformamide or a mixture thereof. Suitably, a strong ammonia solution may be added to the reaction mixture prior to the addition of the activated metal. The temperature of the reaction is usually kept under 0° C., in the range of between −20° C. and +5° C. The desired compound can be isolated and purifed according to known techniques.

This method is very suitable for the preparation of 7-amino-3-methylenecephem-4-carboxylic acid and salts and esters thereof, from the new 7β-(cyclo)-alkylideneammonio-3-halomethyl-3-cephem-4-carboxylic acid derivatives, which are described in European Patent Application No. 87201316.4, filed on July 10, 1987.

The 3-halomethylene cepham compounds which are disclosed in the present invention are believed to be novel and form still another aspect of this invention.

The following Examples are offered by way of illustration and not by way of limitation of the invention. No attempts were made to optimize the yields.

Example 1–6 show the preparation of certain new 3-bromomethyl cephem derivatives. Examples 7–13 illustrate the preparation of 3-phosphoniomethyl cephem compounds and Examples 14–23 the preparation of 3-exomethylene cephams from such phosphonium compounds. Examples 24–30 show "one-pot" syntheses of 3-exomethylene cephams via phosphonium salts, but without isolating these intermediates. Finally, Examples 31–45 illustrate the direct conversion of 3-bromomethyl cephem derivatives with certain metals.

EXAMPLES

Example 1

Preparation of tert-butyl (6R,7R)-3-bromomethyl-1,1-dioxo-7-phenylacetamido-3-cephem-4-carboxylate from tert-butyl (6R,7R)-3-methyl-1,1-dioxo-7-phenylacetamido-3-cephem-4-carboxylate A solution of 6 g (14.27 mmoles) tert-butyl (6R,7R)-3-methyl-1,1-dioxo-7-phenylacetamido-3-cephem-4-carboxylate in 90 ml of methylene chloride was stirred at 0° C. under dry nitrogen with 3.5 g (19.66 mmoles) of N-bromo-succinimide and irradiated with 26 fluorescent tubes (Phillips 03T; 20 W) for 60 minutes. The solution was washed with water (pH=7), combined with a methylene chloride backwash of the aqueous phase, dried and evaporated to low volume. The residue was chromatographed on Kieselgel H type 60 with a preparative Yobin-Yvon column. Eluation with toluene/ethyl acetate (5:1) gave after trituration with ether 1.43 g of the title compound with a purity of 94%.

IR-spectrum (KBr-disc; values in cm$^{-1}$); 3420, 3000, 1790, 1720, 1680, 1600, 1500, 1260, 1230, 1040, 1020, 990, 820, 700 and 680.

PMR-spectrum (360 MHz; CDCl$_3$; tetramethylsilane as an internal reference; δ-values in ppm); 1.54 (s, 9H); 3.64 (s, 2H); 3.72 and 4.08 (ABq, 2H; J=19.0 Hz); 4.19 and 4.48 (ABq, 2H; J=10.8 Hz); 4.81 (d, 1H; J=4.6 Hz); 6.13 (dd, 1H, J=4.6 and 10.2 Hz); 6.78 (d, 1H, J=10.2 Hz); 7.3 (m, 5H).

Example 2

Preparation of 4-nitrobenzyl (1S,6R,7R)-3-bromomethyl-1-oxo-7-phenylacetamidocephem-4-carboxylate from 4-nitrobenzyl (1R,6R,7R)-3-methyl-1-oxo-7-phenylacetamido-3-cephem-4-carboxylate A solution of 1 g (2.1 mmoles) 4-nitrobenzyl (1S,6R,7R)-3-methyl-1-oxo-7-phenylacetamido-3-cephem-4-carboxylate in 100 ml of methylene chloride and 100 ml of acetic acid was stirred at 4° C. under dry nitrogen with 620 mg (3.4 mmoles) of N-bromosuccinimide and irradiated with a 150 W tungsten lamp for 90 minutes. After evaporating the solvents while adding some toluene, the residue was washed with a cold sodium bisulfphite solution, giving 1.0 g of the title product.

PMR-spectrum (360 MHz; CF$_d$COOD; tetramethylsilane as an internal reference; δ-values in ppm); 3.59 and 4.05 (ABq, 2H; J=19 Hz); 3.65 (s, 2H); 4.22 (s,2H); 4.84 (d, 1H; J=4.5 Hz; 5.31, 5.38 (ABq, 2H; J=15.6 Hz); 6.05 (d, 1H; J=4.5 Hz); 7.0–8.2 (m. 9H).

Example 3

Preparation of 4-nitrobenzyl (1S,6R,7R)-3-bromomethyl-1,1-oxo-7-phenoxyacetamido-3-cephem-4-carboxylate from 4-nitrobenzyl (1S,6R,7R)-3-methyl-1-oxo-7-phenoxyacetamido-3-cephem-4-carboxylate A solution of 2.6 g (purity 82: 4.27 mmoles) of 4-nitrobenzyl (1S,6R,7R)-3-methyl-1-oxo-7-phenoxyacetamido-3-cephem-4-carboxylate in 150 ml of methylene chloride and 150 ml of acetic acid was stirred at 0° C. under dry nitrogen with 1.85 g (10.39 mmoles) of N-bromosuccinimide and irradiated with 150 W tungsten lamp for 200 minutes. After evaporating the solvents the residue was dissolved in methylene chloride, the methylene chloride solution was washed with water and phosphate buffer and evaporated. Trituration with ether/petroleum ether 40°–60° C. gave 2.17 g of the title product with a purity of 67% (yield 48%).

PMR-spectrum (360 MHz; DMSO-d$_6$; internal reference tetramethylsilane): 3.81 and 4.02 (ABq, 2H; J=18.5 Hz); 4.53 and 4.59 (ABq, 2H; J=9.8 Hz); 4.67 (s, 2H); 5.06 (d, 1H; J=4.4 Hz); 5.48 (s, 2H); 6.11 (d, 1H; J=4.4 and 9.8 Hz); 6.96 and 7.16 (m, 5H); 7.73 and 8.25 (ABq, 4H; J=8.3 Hz) 8.19 (d, 1H; J=9.8 Hz).

Example 4

Preparation of methyl (1S, 6R,7R)-3-bromomethyl-1-oxo-7-phenoxyacetamido-3-cephem-4-carboxylate from methyl (1S,6R,7R)-3-methyl-1-oxo-7-phenoxyacetamido-3-cephem-4-carboxylate A solution of 2.3 g (6.1 mmoles) of methyl (1S,6R,7R)-3-methyl-1-oxo-7-phenoxyacetamido-3-cephem-4-carboxylate in 50 ml of methylene chloride and 50 ml of acetic acid was stirred at 0° C. under dry nitrogen with 1.5 g of N-bromosuccinimide and irradiated with a 150 W tungsten lamp for 60 minutes. After adding 0.3 ml of tributylphosphite and stirring for 4 hours at −5° C. the reaction mixture was poured out into 500 ml of methylene chloride and 100 ml of water. After separating the layers the organic layer was washed with water (4×100 ml), combined with a methylene chloride backwash (100 ml) of the aqueous phases, dried and evaporated. Trituration of the residue with either gave 2.55 g of the title compound with a purity of 58%. Yield 53%.

IR-spectrum (KBr-disc; values in cm$^{-1}$); 3380, 2955, 1790, 1728, 1697, 1599, 1522, 1495, 1435, 1375, 1305, 1240, 1174, 1098, 1065, 1020, 735 and 690.

PMR-spectrum (360 MHz; CDCl$_3$/DMSO-d$_6$ (3:1); tetramethylsilane as an internal reference; δ-values in ppm): 3.81 and 3.90 (ABq, 2H; J=18.0 Hz); 3.91 (s, 3H); 4.41 and 4.59 (ABq, 2H; J=10.1 Hz); 4.60 (s, 2H); 4.99 (d, 1H; J=4.5 Hz); 6.10 (dd, 1H, J=4.5 and 10.1 Hz); 6.9–7.3 (m, 5H); 8.04 (d, 1H; J=10.1 Hz).

Example 5

Preparation of 4-nitrobenzyl (1S, 6R,7R)-3-bromomethyl-7-formamido-1-oxo-3-cephem-4-carboxylate from 4-nitrobenzyl (1S,6R,7R)-3-methyl-1-oxo-3-cephem-4-carboxylate A solution of 2 g (5.84 mmoles) of 4-nitrobenzyl (1S,6R,7R)-7-formamideo-3-methyl-1-oxo-3-cephem-4-carboxylate in 150 ml of methylene chloride and 150 ml of acetic acid was stirred at 0° C. under dry nitrogen with 1.4 g (7.8 mmoles) of N-bromosuccinimide and irradiated with a 150 W tungsten lamp for 90 minutes. After adding 0.2 ml (0.7 mmoles) of tributylphosphite and stirring for 15 minutes at −5° C. the solvents were evaporated. After dissolving the residue in a mixture of methylene chloride and ethyl acetate and washing with water the solution was concentrated. The crystals were filtered off and washed with ether and petroleum ether 40°–60° C. and dried giving 1.6 g of the title compound with a purity of 79%. Yield 61%.

IR-spectrum (KBr-disc; values in cm$^{-1}$); 3280, 1780, 1730, 1720, 1665, 1522, 1386, 1350, 1260, 1242, 1172, 1030, 852, 739, 696 and 620.

PMR-spectrum (360 MHz; DMSO-d$_6$; tetramethylsilane as an internal reference; δ-values in ppm): 3.82 and 3.98 (ABq, 2H; J=18.0 Hz); 4.52 and 4.62 (ABq, 2H; J=10.2 Hz); 5.03 (d, 1H; J=4.9 Hz); 5.46 and 5.50 (ABq, 2H; J=13.6 Hz); 6.04 (dd, 1H; J=4.9 and 9.8 Hz); 7.73 and 8.25 (ABq, 4H; J=8.7 Hz); 8.16 (s, 1H); 8.44 (d, 1H; J=9.8 Hz).

Example 6

Preparation of tert-butyl (1S, 6R,7R)-3-dibromomethyl-7formamideo-1-oxo-3-cephem-4-carboxylate from tert-butyl (1S,6R,7R)-3-methyl-7-formamido-1-oxo-3-cephem-4-carboxylate A suspension of 6.3 g (20 mmoles) of tert-butyl (1S,6R,7R)-3-methyl-7-formamido-1-oxo-3-cephem-4-carboxylate in 150 ml of methylene chloride was stirred at 4° C. under dry nitrogen with 9.8 g (55 mmoles) of N-bromosuccinimide, gradually added, and irradiated with a 150 W tungsten lamp for 5.5 hours. After washing the reaction mixture with water, treatment with decolourizing carbon and drying, 6.7 g of a crude mixture ml of brominated products was precipitated with petroleum ether 40°–60° C. The precipitate was chromatographed with a Yobin-Yvon column on Kieselgel H in methylene chloride/ethyl acetate (7:3). The appropriate fractions were combined and evaporated, and the residue was triturated with ether to give 2.4 g of the title product.

IR-spectrum (KBr-disc; values in cm$^{-1}$); 3320, 3092, 1798, 1718, 1678, 1610. 1500, 1397, 1373, 1152, 1000, 646.

PMR-spectrum (360 MHz; DMSO-d$_6$; tetramethylsilane as an internal reference: δ-values in ppm): 1.51 (s, 9H); 3.77, 407, 4.17 and 4.47 (ABq, 2H; J=18 Hz); 5.14 (d, 1H); J=5 Hz); 6.08 (dd, 1H, J=5 and 9.5 Hz); 7.32 (s, 1H); 8.26 (S, 1H); 8.65 (d, 1H; J=9.5 Hz).

Example 7

Preparation of (6R,7R)-4-tert-butoxycarbonyl-1,1-dioxo-7-phenylacetamido-3-triphenylphosphoniomethyl-3-cephem bromide from tert-butyl (6R,7R)-3-bromomethyl-1,1-dioxo-7-phenylacetamido-3cephem-4-carbonylate A mixture of 1 g (2 mmoles of tert-butyl (6R,7R)-3-bromomethyl-1,1-dioxo-7-phenylacetamido-3-cephem-4-carboxylate (see Example 1), 20 ml of tetrahydrofuran and 800 mg (3.1 mmoles) of triphenylphosphine was stirred at 40° C. for 3 hours under nitrogen. Centrifugation, washing with ether and drying gave 1.54 g of the title compound with a purity of 85%. Yield 91%.

IR-spectrum (KBr-disc; values in cm$^{-1}$); 3400, 2980, 2855, 1800, 1710, 1690, 1500, 1440, 1370, 1335, 1300, 1155, 1135, 1110, 1000, 840, 750, 720, 692, 540 and 500.

PMR-spectrum (360 MHz; CDCl$_3$; tetramethylsilane as an internal reference: δ-values in ppm): 1.24 (s, 9H); 3.29 (d, 1H; J=19 Hz); 3.62 (s, 2H); 5.13 and 5.75 (2xt, 2H, J=14.4 and 14.4 Hz); 5.14 (d, 1H); J=4.5 Hz); 5.49 (dd, 1H, J=19.0 and 5.4 Hz); 6.12 (dd, 1H; J=4.5 and 10.1 Hz); 6.92 (d, 1H; J=10.1 Hz); 7.2–7.8 (m, 20H).

Example 8

Preparation of (1S,6R,7R)-4-nitrobenzyloxycarbonyl-1-oxo-7-phenylacetamido-3-triphenylphosphoniomethyl-3-cephem bromide from 4-nitrobenzyl (1S,6R,7R)-3-bromomethyl-1-oxo-7-phenylacetamido-3cephem-4-carboxylate A mixture of 447 mg 4-nitrobenzyl (1S,6R,7R)-3-bromomethyl-1-oxo-7-phenylacetamido-3-cephem-4-carboxylate (see Example 2), 600 mg of triphenylphosphine and 15 ml of tetrahydrofruan was stirred at 40° C. for 3 hours. After evaporation of the solvent and addition of ether the precipitate formed was filtered off giving 600 mg of the title product with a purity of 57%.

IR-spectrum (KBr-disc, values in cm$^{-1}$); 3400, 1795, 1724, 1680, 1520, 1438, 1349, 1255, 1170, 1111, 1030, 853, 739, 720, 690 and 500.

PMR-spectrum (360 MHz; CDCl$_3$; tetramethylsilane as an internal reference: δ-values in ppm): 3.50 (d, 1H; J=19.4 Hz); 3.60 (s, 2H); 4.84 (dd, 1H; J=19.4 and 4.5 Hz); 4.98 and 5.11 (ABq, 2H; J=13.3 Hz); 5.10 (d, 1H; J=4.4 Hz); 5.11 and 5.45 (2xt, 2H, J=14.4 and 14.4 Hz); 6.06 (dd, 1H; J=4.4 and 10.1 Hz); 6.94 (d, 1H; J=10.1 Hz); 7.2–8.3 (m, 24H).

Example 9

Preparation of
(1S,6R,7R)-4-nitrobenzyloxycarbonyl-1-oxo-7-phenoxyacetamido-3-triphenylphosphoniomethyl-3-cephem bromide from 4-nitrobenzyl (1S,6R,7R)-3-bromomethyl-1-oxo-7-phenylacetamido-3cephem-4-carboxylate To a solution of 1.73 g (purity 67%; 2 mmoles) of 4-nitrobenzyl (1S,6R,7R)-3-bromomethyl-1-oxo-7-phenoxyacetamido-3-cephem-4-carboxylate (see Example 3), in 55 ml of tetrahydrofuran, 1.58 g (6 mmoles) of triphenylphosphine were added and the mixture was stirred at 40° C. for 3 hours under nitrogen. After standing overnight precipitation with ether gave 2.29 g of the title product with a purity of 59%. Yield 80%.

IR-spectrum (KBr-disc; values in cm$^{-1}$); 3400, 1800, 1725, 1700, 1605, 1592, 1524, 1495, 1442, 1390, 1350, 1300, 1245, 1175, 1114, 1070, 1035, 755, 695 and 510.

PMR-spectrum (360 MHz; CDCl$_3$; tetramethylsilane as an internal reference: δ-values in ppm): 3.51 (d, 1H; J=19.5 Hz); 4.54 (s, 2H); 4.97 (dd, 1H; J=19.5 and 5.9 Hz); 5.00 and 5.14 (ABq, 2H; J=13.2 Hz); 5.13 and 5.51 (2xt, 2H, J=14.6 and 17.1 Hz); 5.21 (d, 1H; J=4.9 Hz); 6.16 (dd, 1H; J=4.9 and 10.7 Hz); 6.94, 7.02 and 7.29 (m, 5H); 7.44 and 8.18 (ABq, 4H; J=8.8 Hz); 7.5–7.9 (m, 15H).

Example 10

Preparation of
(1S,6R,7R)-4-methoxycarbonyl-1-oxo-7-phenoxyacetamido-3-triphenylphosphoniomethyl-3-cephem bromide from methyl (1S,6R,7R)-3-bromomethyl-1-oxo-7-phenoxyacetamido-3-cephem-4-carboxylate A mixture of 1.37 g (purity 58%; 1.74 mmoles) of methyl (1S,6R,7R)-3-bromomethyl-1-oxo-7-phenoxyacetamido-3-cephem-4-carboxylate (see Example 4), 1.18 g (4.5 mmoles) of triphenylphosphine and 15 ml of tetrahydrofuran was stirred at 40° C. for 3 hours. After addition of ether the precipitate formed was isolated by centrifugation, giving 1.93 g of the title product with a purity of 64%. Yield 99%.

IR-spectrum (KBr-disc; values in cm$^{-1}$); 3390, 1795, 1720, 1691, 1530, 1490, 1438, 1370, 1297, 1260, 1240, 1170, 1110, 1028, 750, 720, 690 and 500.

PMR-spectrum (360 MHz; CDCl$_3$; tetramethylsilane as an internal reference: δ-values in ppm): 3.56 (s, 3H); 3.57 (d, 1H; J=19.0 Hz); 4.54 (s, 2H); 4.88 (dd, 1H; J=19.0 and 5.9 Hz); 5.09 and 5.52 (2xt, 2H, J=14.6 and 17.1 Hz); 5.20 (d, 1H; J=4.9 Hz); 6.13 (dd, 1H; J=4.9 and 10.3 Hz); 6.93, 7.02 and 7.29 (m, 5H); 7.6–8.0 (m, 15H).

Example 11

Preparation of
(1S,6R,7R)-4-diphenylmethyloxycarbonyl-1-oxo-7formamido-3-triphenylphosphoniomethyl-3-cephem bromide from diphenylmethyl (1S,6R,7R)-3-bromomethyl-7-formamido-1-oxo-3-cephem-4-carboxylate A mixture of 2 g (purity 74%; 2.94 mmoles) of diphenylmethyl (1S,6R,7R)-3-bromomethyl-7-formamido-1-oxo-3-cephem-4-carboxylate (see U.S. Pat. No. 3,769,277), 3 g of triphenylphosphine and 50 ml of tetrahydrofuran was stirred at 40° C. for 16 hours and treated with ether, giving 2.97 g of the title product with a purity of 73%. Yield 96%.

IR-spectrum (KBr-disc; values in cm$^{-1}$); 3400, 3060, 2970, 2860, 1795, 1690, 1500, 1460, 1370, 1250, 1160, 1110, 745, 690 and 500.

PMR-spectrum (360 MHz; CDCl$_3$; tetramethylsilane as an internal reference: δ-values in ppm): 3.60 (d, 1H; J=19.1 Hz); 4.97 (dd, 1H; J=19.1 and 5.4 Hz); 5.17 and 5.49 (2xt, 2H, J=14.7 and 14.1 Hz); 5.21 (d, 1H; J=4.9 Hz); 6.14 (dd, 1H; J=4.9 and 10.3 Hz); 6.48 (s, 1H); 7.02 (d, 1H; J=10.3 Hz); 7.1–7.9 (m, 25H); 8.17 (s, 1H).

Example 12

Preparation of
(1S,6R,7R)-4-tert-butoxycarbonyl-1-oxo-7-phenylacetamido-3-triphenylphosphoniomethyl-3-cephem bromide from tert-butyl (1S,6R,7R)-3-bromomethyl-1-oxo-7-phenoxyacetamido-3-cephem-4-carboxylate 24.2 g (purity 89%; 44.6 mmoles) of tert-butyl (1S,6R,7R)-3-bromomethyl-1-oxo-7-phenylacetamido-3-cephem-4-carboxylate was heated in 250 ml of tetrahydrofuran at 40° C. After addition of 4.4 g (55 mmoles) of triphenylphosphine stirring was continued for 2 hours and then 250 ml of diethylether was added. Filtration of the precipitate, washing with diethylether and drying gave 37.3 g of the title compound with a purity of 84%. Yield 94%.

IR-spectrum (KBr-disc; values in cm$^{-1}$); 1795, 1710, 1690, 1620, 1505, 1445, 1365, 1310, 1280, 1265, 1160, 1115, 1040, 1005, 840, 745, 725 and 700.

PMR-spectrum (360 MHz; CDCl$_3$; δvalues in ppm; tetramethylsilane as an internal reference): 1.23 (s, 9H); 3.41 (dd, 1H; J=18.7 and 2.0 Hz); 3.58 (s, 2H); 4.87 (dd, 1H; J=18.7 and 5.4 Hz); 4.95 (d, 1H; J=5.0 Hz); 5.14 (dd, 1H; J=14.4 and 17.6 Hz); 5.48 (dd, 1H; J=14.4 and 13.7 Hz); 6.06 (dd, 1H: J=5.0 and 10.1 Hz); 6.76 (d, 1H; J=10.1 Hz); 7.2–7.9 (m, 20H).

Example 13

Preparation of
(6R,7R)-4-tert-butoxycarbonyl-1-oxo-7-phenyl-3-triphenylphosphoniomethyl-3-cephem bromide from (1S,6R,7R)-4-tert-butoxycarbonyl-1-oxo-7-phenylacetamido-3triphenylphosphoniomethyl-3-cephem bromide To suspension of 1.85 g (2.23 mmoles) of (1S,6R,7R)-4-tert-butoxycarbonyl-1-oxo-7-phenylacetamido-3-triphenylphosphoniomethyl-3-cephem bromide (see Example 12), in 25 ml of tetrahydrofuran was added 0.35 ml (4 mmoles) of phosphorous trichloride at 0° C. After 30 minutes 20 ml of water was added to the clear reaction mixture, the pH was adjusted to 5 with a 4 N sodium hydroxide solution and stirring was continued for 45 minutes maintaining the pH at 5. After adding 20 ml of ethyl acetate, separation of the layers and extracting the water layer with 2×10 ml of ethyl acetate, the combined organic layers were dried (magnesium acetate) and evaporated to dryness. Isolation by trituration and drying gave 1.73 g of the title product. Purity 82%. Yield 87%.

IR-spectrum (KBr-disc; values in cm$^{-1}$); 1786, 1710, 1676, 1630, 1540, 1445, 1380, 1310, 1280, 1160, 1115, 1010, 845, 730 and 700.

PMR-spectrum (360 MHz; CDCl$_3$; δ-values in ppm; tetramethylsilane as an internal reference): 1.22 (s, 9H); 3.10 (dd, 1H; J=18.9 and 2.1 Hz); 3.98 (dd, 1H; J=18.9 and 5.9 Hz); 3.63 and 3.70 (ABq, 2H, J=14.7 Hz); 4.79 (d, 1H; J=4.6 Hz); 5.01 and 5.29 (2xtr, 2H, J=14.6 and 14.7 and 13.9 Hz); 5.62 (dd, 1H; J=4.6 and 8.8 Hz); 7.1–7.8 (m, 20H).

Example 14

Preparation of tert-butyl (1S,6R,7R)-3-methylene-1,1-dioxo-7-phenylacetamidocepham-4-carboxylate from (6R,7R)-4-tert-butoxycarbonyl-1,1-dioxo-7-phenylacetamido-3-triphenylphosphoniomethyl-3-cephem bromide A suspension of 385 mg of stannous chloride dihydrate in 5 ml of water, of which the pH was adjusted to 9 with a 4 N sodium hydroxide solution was added to a suspension of 765 mg (purity 85%; 0.85 mmoles) of (6R,7R)-4-tert-butoxycarbonyl-1,1-dioxo-7-phenylacetamido-3-triphenyl-phosphoniomethyl-3-cephem bromide (see Example 7) in 15 ml of tetrahydrofuran. The reaction mixture was stirred at 40° C. for 90 minutes, while maintaining the pH at 9 and adjusting the pH to 7 when the reaction was terminated, and poured out into ethyl acetate. After washing the organic layer with brine the solvents were evaporated. The residue was dissolved in acetone and ether and petroleum ether 40°–60° C. were added giving 510 mg of a mixture of the title compound (yield 45%) and the starting compound (25%), as confirmed with PMR spectroscopy.

Example 15

Preparation of 4-nitrobenzyl (1S,4R,6R,7R)-3-methylene-1-oxo-7-phenylacetamidocepham-4-carboxylate from (1S,6R,7R)-4-nitrobenzyloxycarbonyl-1-oxo-7-phenylacetamido-3-triphenylphosphoniomethyl-3-cephem bromide A suspension of 265 mg of stannous chloride dihydrate in 5 ml of water, of which the pH was adjusted to 9.5 with a 4 N sodium hydroxide solution was added to a suspension of 548 mg (purity 57%; 0.38 mmoles) of (1S,6R,7R)-4-nitrobeznyloxycarbonyl-1-oxo-7-phenylacetamido-3-tri-phenylphosphoniomethyl-3-cephem bromide (see Example 8) in 15 ml of tetrahydrofuran. The reaction mixture was stirred at 40° C. for 90 minutes, while maintaining the pH at 9 and adjusting the pH to 7 when the reaction was terminated, and poured out into ethyl acetate. The organic layer was washed with water (4×) and brine, combined with an ethyl acetate backwash of the aqueous phase and evaporated. The residue was dissolved in acetone and treated with ether and petroleum ether 40°–60° C., giving the title product after centrifugation. The structure was confirmed by PMR spectroscopy.

PMR-spectrum (360 MHz; DMSO-$d_6$; tetramethylsilane as an internal reference; δ-values in ppm): 3.51 and 3.64 (ABq, 2H; J=15.6 Hz); 3.71 and 3.89 (ABq, 2H; J=14.4 Hz); 5.01 (d, 1H; J=4.5 Hz); 5.32, 5.39 and 5.72 (3xs, 3H); 5.47 (s, 2H); 7.1–8.3 (m, 10H).

Example 16

Preparation of methyl (1S,4R,6R,7R)-7-phenoxyacetamido-3-methylene-1-oxocepham-4-carboxylate from (1S,6R,7R)-4-methoxycarbonyl-1-oxo-7-phenylacetamido-3-triphenylphosphoniomethyl-3-cephem bromide A suspension of 385 mg of stannous chloride dihydrate in 5 ml of water, of which the pH was adjusted to 9.5 with a 4 N sodium hydroxide solution was added to a suspension of 720 mg (purity 64%; 0.64 mmoles) of (1S,6R,7R)-4-methoxycarbonyl-1-oxo-7-phenoxyacetamido-3-triphenylphosphoniomethyl- 3-cephem bromide (see Example 10) in 15 ml of tetrahydrofuran. The reaction mixture was stirred at 40° C. for 90 minutes, while maintaining the pH at 9 and adjusting the pH to 7 when the reaction was terminated, and poured out into ethyl acetate. The organic layer was washed with water (4×) and brine, combined with an ethyl acetate backwash of the aqueous phase and evaporated. The residue was dissolved in acetone and treated with ether and petroleum ether 40°–60° C., giving the title product after centrifugation. The structure was confirmed by PMR spectroscopy.

PMR-spectrum (360 MHz; DMSO-$d_6$; tetramethylsilane as an internal reference; δ-values in ppm): 3.70 (s, 3H); 3.79 and 3.93 (ABq, 2H; J=14.2 Hz); 4.62 (s, 2H); 5.11 (d, 1H; J=4.4 Hz); 5.34, 5.41 and 5.71 (3xs, 3H); 5.80 (dd, 1H; J=4.4 and 10.2 Hz); 6.9–7.6 (m, 5Hz); 8.27 (d, 1H, J=10.2 Hz).

Example 18

Preparation of diphenylmethyl (1S,4R,6R,7R)-7-formamido-3-methylene-1-oxocepham-4-carboxylate from (1S,6R,7R)-4diphenylmethyloxycarbonyl-1-oxo-7-formamido-3-triphenyl-phosphoniomethyl-3-cephem bromide A suspension of 385 mg of stannous chloride dihydrate in 5 ml of water, of which the pH was adjusted to 9.5 with a 4 N sodium hydroxide solution was added to a suspension of 765 mg (purity 73%; 0.73 mmoles) of (1S,6R,7R)-4-diphenylmethyloxycarbonyl-1-oxo-7-formamido-3-triphenyl-phosphoniomethyl-3-cephem bromide (see Example 11) in 15 ml of tetrahydrofuran. The reaction mixture was stirred at 40° C. for 90 minutes, while maintaining the pH at 9 and adjusting the pH to 7 when the reaction was terminated, and poured out into ethyl acetate (100 ml). The organic layer was washed with water, combined with an ethyl acetate backwash of the aqueous phase and evaporated. The residue was dissolved in acetone and treated with ether and petroleum ether 40°–60° C., giving after centrifugation 260 mg of a mixture of the title product and triphenylphosphine oxide containing 53.4% of the title product. Yield 45%.

Example 19

Preparation of tert-butyl (1S,4R,6R,7R)-3-methylene-1-oxo-7-phenylacetamidocepham-4-carboxylate from (1S,6R,7R)-4-tert-butoxy-carbonyl-1-oxo-7-phenylacetamido-3-triphenylphosphoniomethyl-3-cephem bromide in the presence of stannous chloride dihydrate To a suspension of 750 mg (purity 84%; 0.84 mmoles) of (1S,6R,7R)-4-tert-butoxycarbonyl-1-oxo-7-phenylacetamido-3-triphenylphosphoniomethyl-3-cephem bromide (see Example 12) in 15 ml of tetrahydrofuran was added a suspension having a pH of 9 prepared by adding a 4 N sodium hydroxide solution to 385 mg of stannous chloride dihydrate in 5 ml of water. After heating the reaction mixture to 60° C. and maintaining the pH at 9 with a 1 N sodium hydroxide solution the reaction mixture was stirred for 20 minutes and cooled down to room temperature. After adjusting the pH to 7 and pouring out the reaction mixture into 60 ml of ethyl acetate the layers were separated, the water layer extracted with 3×30 ml of ethyl acetate and the combined organic layers were washed with brine. The ethyl acetate solution, containing 96% of the title compound as determined by HPLC analysis, was concentrated to dryness. The residue was then dissolved in acetone and precipitated with diethylether and petroleum ether 40°-60° C. Isolation by centrifugation, washing and drying gave 470 mg of the title compound with a purity of 68%. Yield 94%.

Example 20

Preparation of tert-butyl (1S,4R,6R,7R)-3-methylene-1-oxo-7-phenylacetamidocepham-4carboxylate from (1S,6R,7R)-4-tert-butoxycarbonyl-1oxo-phenylacetamido-3-triphenylphosphoniomethyl-3-cephem bromide A. The process according to Example 19 was repeated without addition of stannous chloride dihydrate. The reaction was carried out at 35° C. for 2 hours while maintaining the pH at 9. The yield in solution was 39%. After isolation 200 mg of the title compound was obtained with a purity of 20%. Isolated yield: 12%.

B. The process according to Example 19 was repeated but, instead of stannous chloride dihydrate, 400 mg of stannous bromide was used. The reaction was carried out at 35° C. for 90 minutes. The yield in solution was 92%. After isolation 540 mg of the title compound was obtained with a purity of 55%. Isolated yield: 87%.

C. The process according to Example 19 was repeated but, instead of stannous chloride dihydrate, 0.2 ml of stannous bromide was used. The reaction was carried out at 35° C. for 2 hours. The yield in solution was 82%. After isolation 370 mg of the title compound was obtained with a purity of 70%. Isolated yield: 76%.

D. The process according to Example 19 was repeated but, instead of stannous chloride dihydrate, 250 mg of disodium hydrogen phosphate was used. The reaction was carried out at 35° C. for 2 hours. The yield in solution was 88%. After isolation 360 mg of the title compound was obtained with a purity of 77%. Isolated yield: 82%.

E. The process according to Example 19 was repeated but, instead of stannous chloride dihydrate, 680 mg of a solid residue containing sodium stannite was used which was prepared in the following manner: a solution of 450 mg of stannous chloride dihydrate in 80 ml of a 0.1 N sodium hydroxide solution was concentrated to dryness giving 800 mg of the residue mentioned. After treating a suspension of the starting material in tetrahydrofuran with 680 mg of this residue at 40° C. for 1 hour, 570 mg of the title compound was obtained with a purity of 48% after isolation. Isolated yield: 80%.

F. The process according to Example 19 was repeated but, instead of stannous chloride, sodium stannite was used which was formed in situ by adding to the suspension of the cephem bromide compound (750 mg) in 15 ml of tetrahydrofuran a solution of 385 mg of stannous chloride dihydrate and 100 mg of sodium chloride in 5 ml of water, of which the pH was adjusted to 9 with a 4 N sodium hydroxide solution. After heating the reaction mixture up to 40° C. and maintaining the pH at 9 with a 1 N sodium hydroxide solution, the reaction mixture was stirred for 90 minutes and cooled down to room temperature. After adjusting the pH to 7 and pouring out the reaction mixture into 60 ml of ethyl acetate the layers were separated, the water layer extracted with 3×30 ml of ethyl acetate and the combined organic layers were washed with brine. The ethyl acetate solution, containing 92% of the title compound as determined by HPLC analysis was concentrated to dryness. The residue was then dissolved in acetone and precipitated with diethylether and petroleum ether 40°-60° C. Isolation by centrifugation, washing and drying gave 490 mg of the title compound with a purity of 61%. Yield 88%.

G. The process according to Example 19 was repeated but, instead of stannous chloride dihydrate, 175 mg of sodium bromide was used. The reaction was carried out at 35° C. for 2 hours. The yield in solution was 86%. After isolation 360 mg of the title compound was obtained with a purity of 51%. Isolated yield: 79%.

H. The process according to Example 19 was repeated but, instead of stannous chloride dihydrate, 100 mg of sodium chloride was used. The reaction was carried out at 35° C. for 90 minutes. The yield in solution was 86%. After isolation 610 mg of the title compound was obtained with a purity of 44%. Isolated yield: 79%.

I. The process according to Example 19 was repeated but, instead of stannous chloride dihydrate, 230 mg of aluminum chloride was used. The reaction was carried out at 40° C. for 90 minutes. The yield in solution was 83%. After isolation 600 mg of the title compound with a purity of 46%. Isolated yield: 81%.

J. The process according to Example 19 was repeated but, instead of stannous chloride dihydrate, 0.14 ml of boron trichloride was used. The reaction was carried out at 35° C. for 2 hours. The yield in solution was 77%. After isolation 370 mg of the title compound was obtained with a purity of 65%. Isolated yield: 67%.

K. The process according to Example 19 was repeated but, instead of stannous chloride dihydrate, 0.14 ml of phosphorus trichloride was used. The reaction was carried out at 35° C. for 2 hours. The yield in solution was 84%. After isolation 380 mg of the title compound was obtained with a purity of 73%. Isolated yield: 82%.

L. The process according to Example 19 was repeated but, instead of stannous chloride dihydrate, 250 mg of zinc chloride was used. The reaction was carried out at 40° C. for 90 minutes. The yield in solution, determined according to HPLC, was 88%. After isolation 531 mg of the title compound was obtained with a purity of 53%. Isolated yield: 82%.

M. The process according to Example 19 was repeated but, instead of stannous chloride dihydrate, 435 mg of tellurium tetrachloride was used. The reaction was carried out at 30° C. for 2 hours. After isolation 302 mg of the title compound was obtained with a purity of 48%. Isolated yield: 57%.

N. The process according to Example 19 was repeated but the added suspension of stannous chloride dihydrate was adjusted to pH 12 by adding a 4 N sodium hydroxide solution to 385 mg of stannous chloride dihydrate in 5 ml of water and stirring this mixture for 15 minutes. After heating the reaction mixture to 40° C. and maintaining the pH at 10.5 with a 1 N sodium hydroxide solution, the reaction mixture was stirred for 45 minutes and poured out into ethyl acetate. After adjusting the pH to 7, separating the layers and evaporating the organic solvent to dryness the residue was treated with acetone, diethylether and petroleum ether 40°-60° C. After collecting and drying the solid 500 mg of the title compound with a purity of 68% was obtained. Yield 100%.

Example 21

Preparation of tert-butyl (1S,4R,6R,7R)-3-methylene-1-oxo-7-phenylacetamidocepham-4-carboxylate from (1S,6R,7R)-4-tert-butoxycarbonyl-1-oxo-7-phenylacetamido-3-triphenylphosphoniomethyl-3-cephem bromide A. To a solution of 750 mg (purity 84%; 0.84 mmoles) of (1S,6R,7R)-4-tert-butoxycarbonyl-1-oxo-7-phenylacetamido-3-triphenylphosphoniomethyl-3-cephem bromide (see Example 12) in 15 ml of tetrahydrofuran was added a suspension having a pH of 9 prepared by adding a 4 N sodium hydroxide solution to 385 mg of stannous chloride dihydrate in 5 ml of water. After heating the reaction mixture to 40° C. and maintaining the pH at 9 with a 1 N sodium hydroxide solution to reaction mixture was stirred for 90 minutes and cooled down to room temperature. After centrifugation and extracting the residue with ethyl acetate (2×), the organic solution, containing 66% of the title compound as determined by HPLC analysis, was washed with brine, dried and concentrated to dryness. Then the residue was treated with acetone, diethylether and petroleum ether 40°-60° C. After collecting and drying the solid 540 mg of the title compound with a purity of 35% was obtained. Yield 56%.

B. To a solution of 1.5 g (purity 84%; 1.68 mmoles) of (1S,6R,7R)-4-tert-butoxycarbonyl-1-oxo-7-phenylacetamido-3-triphenylphosphoniomethyl-3-cephem bromide (see Example 12) in 30 ml of methylene chloride was added a suspension having a pH of 9 prepared by adding a 4 N sodium hydroxide solution to 770 mg of stannous chloride dihydrate in 10 ml of water. After heating the reaction mixture up to 40° C. and maintaining the pH at 9 with a 1 N sodium hydroxide solution the reaction mixture was stirred for 90 minutes and poured out into ethyl acetate. After separation of the layers the organic layer was washed with brine and concentrated to dryness. Then the residue was dissolved in acetone and treated with petroleum ether. After collecting and drying the solid 1.08 g of the title compound with a purity of 21% was obtained. Yield 33%.

Example 22

Preparation of tert-butyl (4R,6R,7R)-3-methylene-7-phenylacetamidocepham-4-carboxylate from (6R,7R)-4-tert-butoxycarbonyl-7-phenylacetamido-3-triphenylphosphoniomethyl-3-cephem bromide To a stirred mixture of 729 mg (purity 79%; 0.79 mmoles) of (6R,7R)-4-tert-butoxycarbonyl-7-phenylacetamido-3-triphenylphosphoniomethyl-3-cephem bromide in 15 ml of tetrahydrofuran was added under nitrogen a solution of 385 mg of stannous chloride dihydrate in 5 ml of water, of which the pH was adjusted to 9. After raising the temperature to 40° C. the pH was maintained at 9-9.5 for 90 minutes. The reaction mixture was poured out into ethyl acetate, the layers were separated and the amount of the title product formed was determined in the organic layer. Yield 95%.

Example 23

Preparation of tert-butyl (4R,6R,7R)-3-methylene-7-phenylacetamidocepham-4-carboxylate from tert-butyl (1S,6R,7R)-3bromomethyl-1-oxo-7-phenylacetamido-3-cephem-4-carboxylate To a solution of 5 g (purity 89%; 9.2 mmoles) of tert-butyl (1S,6R,7R)-3-bromomethyl-1-oxo-7-phenylacetamido-3-cephem-4-carboxylate in 150 ml of tetrahydrofuran was added 4 g (15.3 mmoles) of triphenylphosphine with stirring at 40° C.

While stirring continuously at 40° C. gradually a white precipitate, the phosphonium salt, was formed. After 2 hours the suspension was cooled down to 2° C. and treated with 1.3 g (14.9 mmoles) of phosphorus trichloride. After stirring for 90 minutes at 2° C. and adjusting the pH of the clear solution to 9.5 with a 4 N sodium hydroxide solution, the reaction mixture was stirred for 60 minutes at 30° C.

After adjusting the pH to 6.8 with 1 N hydrochloric acid solution the reaction mixture was extracted twice with a total amount of 400 ml of ethyl acetate. Evaporation of the dried (magnesium sulphate) organic layer and purification of the organic residue by silica-gel chromatography (toluene/butylacetate 4:1 (v/v)) gave two fractions. After evaporation to dryness and trituration with diethylether the second fraction gave 1.81 g (a yield of 50%) of the title product.

IR-spectrum (KBr-disc; values in cm$^{-1}$): 3300, 1780, 17,42, 1670, 1550, 1382, 1340, 1280, 1160, 940, 735 and 710.

PMR-spectrum (360 MHz; CDCl$_3$; δ-values in ppm; tetramethylsilane as an internal reference): 1.45 (s, 9H); 3.15 and 3.63 (2xd, 2H, J=13.2 Hz); 3.61 (s, 1H); 4.92 and 5.17 (3s, 3H); 5.36 (d, 1H; J=4.3 Hz); 5.64 (d, 1H; J=4.3 Hz); 6.34 (d, 1H; J=9.6 Hz); 7.30 (m, 5H).

Example 24

Preparation of tert-butyl (1S,4R,6R,7R)-3-methylene-1-oxo-7-phenylacetamidocepham-4-carboxylate from tert-butyl (1S,6R,7R)-3bromomethyl-1-oxo-7-phenylacetamido-3-cephem-4-carboxylate To a clear solution of 5 g (purity 89%; 9.2 mmoles) of tert-butyl (1S,6R,7R)-3-bromomethyl-1-oxo-7- phenylacetamido-3-cephem-4-carboxylate in 150 ml of tetrahydrofuran was was added 3.9 g (15 mmoles) of triphenylphosphine under nitrogen. After stirring for 3 hours at 40° C., a suspension having a pH of 9.5 prepared by adding a 4 N sodium hydroxide solution to 3.85 g of stannous chloride in 50 ml of water was added and stirring was continued for 90 minutes, the pH being maintained at 9.5 and the temperature at 40° C. After pouring out the reaction mixture into 200 ml of ethyl acetate, separation of the layers and extraction of the water layer (3×) with ethyl acetate, the combined organic layers were washed with brine. According to a quantitative HPLC-analysis the yield of the title compound in the ethyl acetate solution was 98%. After concentration of the solution in vacuo, treatment with decolourizing carbon and filter aid and evaporation of the solvent, the residue was dissolved in methylene chloride. Precipitation with diethylether and petroleum ether 40°-60° C., filtration of the precipitate, washing and drying gave 6.31 g of the title product with a purity of 41.5%. The yield of the title product was 93%.

Example 25

Preparation of tert-butyl (1S,4R,6R,7R)-3-methylene-1-oxo-7-phenylacetamidocepham-4-carboxylate from tert-butyl (1S,6R,7R)-3bromomethyl-7-[(2-bromo-2-phenyl)acetamido]-1oxo-3-cephem-4-carboxylate To a suspension of 565 g of tert-butyl (1S,6R,7R)-3-bromomethyl-7-[(2-bromo-2-phenyl)acetamido]-1-oxo-3-cephem-4-carboxylate in 15 ml of tetrahydrofuran was added 720 mg of triphenylphosphine under nitrogen. After stirring for 2 hours at 40° C. a suspension having a pH of 9.5 prepared by adding a 4 N sodium hydroxide solution to 385 mg of stannous chloride dihydrate in 5 ml of water was added and stirring was continued for 90 minutes, the pH being maintained at 9.5 and the reaction temperature at 40° C. After pouring out the reaction mixture into ethyl acetate, separation of the layers and extraction of the water layer (3×) with ethyl acetate the combined organic layers were washed with brine. According to a quantitative HPLC-analysis the yield of the title compound in the ethyl acetate solution was 30%. After concentrating the solution to dryness the residue was dissolved in acetone. Precipitation with diethylether and petroleum ether 40°-60° C., filtration of the precipitate, washing and drying gave 750 mg of the title product with a purity of 15%. The yield of the title product was 27%.

Example 26

Preparation of tert-butyl (1S,4R,6R,7R)-3-methylene-1,1-dioxo-7-phenylacetamidocepham-4-carboxylate from tert-butyl (6R,7R)-3bromomethyl-1,1-dioxo-7-phenylacetamido-3-cephem-4-carboxylate To a solution of 240 mg (0.48 mmoles) of tert-butyl (6R,7R)-3-bromomethyl-1,1-dioxo-7-phenylacetamido-3-cephem-4-carboxylate (see Example 1) in 15 ml of tetrahydrofuran was added 262 mg (1 mmole) of triphenylphosphine. The reaction mixture was stirred at 40° C. for 16 hours and then a suspension of 185 mg of stannous chloride dihydrate into 5 ml of water, of which the pH was adjusted to 9 with a 4 N sodium hydroxide solution, was added. After stirring for 90 minutes while maintaining the pH at 9 with a 1 N sodium hydroxide solution the pH was adjusted to 7. The reaction mixture was poured out into ethyl acetate. After washing the organic layer with water and brine the solvents were evaporated The residue was dissolved in acetone and ether, and petroleum ether 40°-60° C. was added giving, after centrifugation and drying 190 mg of the title compound with a purity of 59%. Yield 60%.

Example 27

Preparation of tert-butyl (1S,4R,6R,7R)-7-formamido-3-methylene-1-oxocephem-4-carboxylate from tert-butyl (1S,6R,7R)-3-bromomethyl-7-formamido-1-oxo-3-cephem-4-carboxylate To a stirred solution of 200 mg (0.5 mmoles) of tert-butyl (1S,6R,7R)-3-bromomethyl-7-formamido-1-oxo-3-cephem-4-carboxylate in 15 ml of tetrahydrofuran was added 400 mg of triphenylphosphine. After stirring for 5 hours at 40° C. a suspension having a pH of 9 was prepared by adding a 4 N sodium hydroxide solution to 200 mg of stannous chloride dihydrate in 5 ml of water. Maintaining the pH at 9 with a 1 N sodium hydroxide solution, the reaction mixture was stirred for 90 minutes at 40° C. and cooled down to room temperature. After adjusting the pH at 7 and pouring out the reaction mixture into ethyl acetate the layers were separated, the water layer extracted with ethyl acetate (3×) and the combined organic layers washed with brine. Concentrating the ethyl acetate solution to dryness yielded 242 mg of the title product with a purity of 46% and containing 47% triphenylphosphine oxide. The yield was 52%.

Example 28

Preparation of 4-nitrobenzyl (1S,4R,6R,7R)-7-formamido-3-methylene-1-oxo-3-cephem-4-carboxylate from 4-nitrobenzyl (1S,6R,7R)-3bromomethyl-7-formamido-1-oxo-3-cephem-4-carboxylate To a suspension, prepared by adding 530 mg (2.0 mmoles) of triphenylphosphine to 475 mg (purity 79%; 0.79 mmoles) of 4-nitrobenzyl (1S,6R,7R)-3-bromomethyl-7 formamido-1-oxo-3-cephem-4-carboxylate (see Example 5) in 15 ml of tetrahydrofuran and stirring for 6 hours to 40° C., was added a suspension of 385 mg of stannous chloride dihydrate in 5 ml of water, of which the pH was adjusted to 9.5 with a 4 N sodium hydroxide solution. The reaction mixture was stirred at 40° C. for 90 mins. out into ethyl acetate. The organic layer was washed with water (4×) and brine, combined with an ethyl acetate backwash of the aqueous phase and evaporated. The residue was dissolved in acetone and treated with ether and petroleum ether 40°-60° C., giving after centrifugation the title product. Its structure was confirmed by PMR spectroscopy.

PMR-spectrum (360 MHz: DMSO-$d_6$; tetramethylsilane as an internal reference; δ-values in ppm): 3.82 and 3.95 (ABq, 2H; J=14.4 Hz); 5.09 (d, 1H; J=4.4 Hz); 5.34, 5.49 and 5.74 (3xs, 3H); 5.42 (s, 2H); 5.73 (dd, 1H; J=4.4 and 10.2 Hz).

Example 29

Preparation of methyl (1S,4R,6R,7R)-7-phenoxyacet-amido-3-methylene-1-oxocepham-4-carboxylate from methyl (1S,6R,7R)-3-bromomethyl-1-oxo-7-phenylacetamido-3-cephem-4-carboxylate To a suspension, prepared by adding 390 mg (1.5 mmoles) of triphenylphosphine to 460 mg of methyl (1S,6R,7R)-3-bromomethyl-1-oxo-7-phenyloxyacetamido-3-cephem-4-carboxylate (see Example 4) in 15 ml of tetrahydrofuran, was added a suspension of 385 mg of stannous chloride dihydrate in 5 ml of water, of which the pH was adjusted to 9.5 with a 4 N sodium hydroxide solution. The reaction mixture was stirred at 40° C. for 90 minutes, while maintaining the pH at 9. Then after adjusting the pH to 7 the reaction mixture was poured out into ethyl acetate. The organic layer was washed with water (4×) and brine, combined with an ethyl acetate backwash of the aqueous phase and evaporated. The residue was dissolved in acetone and treated with ether and petroleum ether 40°-60° C., giving after centrifugation the title product. Its structure was confirmed by PMR spectroscopy.

PMR-spectrum (360 MHz: DMSO-$d_6$; tetramethylsilane as an internal reference; δ-values in ppm): 3.70 (s, 3H); 3.79 and 3.93 (ABq, 2H; J=14.2 Hz); 4.62 (s, 2H); 5.11 (d, 1H; J=4.4 Hz); 5.34, 5.41 and 5.71 (3xs, 3H); 5.80 (dd, 1H; J=4.4 and 10.2 Hz); 6.9–7.6 (m, 5H); 8.27 (d, 1H; J=10.2 Hz).

Example 30

Preparation of diphenylmethyl (1S,4R,6R,7R)-7-formamido-3-methylene-1-oxocepham-4-carboxylate from diphenylmethyl (1S,6R,7R)-3-bromomethyl-7formamido-1-oxo-3-cephem-4-carboxylate To a mixture of 500 mg (purity 74%; 0.74 mmoles) of diphenylmethyl (1S,6R,7R)-3-bromomethyl-7-formamidodioxo-7-phenylacetamido-3-cephem-3-4-carboxylate (see U.S. Pat. No. 3,769,277), 780 mg of triphenylphosphine and 15 ml of tetrahydrofuran, a suspension of 385 mg of stannous chloride dihydrate in 5 ml of water was added, of which the pH was adjusted to 9.5 with a 4N sodium hydroxide solution. The reaction mixture was stirred at 40° C. for 90 minutes, while maintaining the pH at 9. Then after adjusting the pH to 7 the reaction mixture was poured out into ethyl acetate (100 ml). The organic layer was washed with water, combined with an ethyl acetate backwash of the aqueous phase and evaporated. The residue was dissolved in acetone and treated with ether and petroleum ether 40°-60° C., giving after centrifugation 550 mg of a mixture of the title product and triphenylphosphine oxide containing 37% of the title product. Yield 64%.

Example 31

Preparation of tert-butyl 7-phenylacetamido-3exomethylene-cepham-4-carboxylate from tert-butyl 7-phenylacetamido-3-bromomethyl-3-cephem-4-carboxylate To a stirred mixture of 4.7 g (purity 92%, 9.2 mmoles) of tert-butyl 7-phenylacetamido-3-bromomethyl-3-cephem-4-carboxylate, 75 ml of dimethylformamide, 2 ml of isobutanol and 10 g of ammonium chloride, 5 g of activated zinc powder at 0° C. was added. After stirring for 2 hours at 0° C., filtration and diluting with ethyl acetate, the reaction mixture was subsequently washed with 300 ml of water, 50 ml of a 1 N hydrolic acid solution, a sodium bicarbonate solution and twice with brine. After drying with magnesium sulphate the ethyl acetate layer was concentrated and triturated with diethylether and a little petroleum ether (40°-60° C.). The precipitate was filtered off and washed with petroleum ether giving 3.49 g of the title compound. Purity 95.3%. Yield 96.2%.

IR-spectrum (KBr-disc; values in cm$^{-1}$): 3320, 2990, 1770, 1723, 1660, 1500, 1390, 1375, 1345, 1260, 1212, 1157, 1032, 934, 860, 800, 750, 736, 700, 575 and 547.

NMR-spectrum (360 MHz; CDCl$_3$; δ-values in ppm, tetramethylsilane as an internal reference): 1.45 (s, 9H); 3.15 and 3.63 (2xd, 2H; J=13.2 Hz); 3.61 (s, 2H); 4.92 and 5.17 (2xs, 3H); 5.36 (d, 1H; J=13.2 Hz); 5.64 (dd, 1H; J=4.3 and 9.6 Hz); 6.34 (d, 1H; J=9.6 Hz); 7.30 (m, 5H).

Example 32

Preparation of tert-butyl (1S,4R,6R,7R)-3-methylene-1-oxo-7-phenylacetamidocepham-4-carboxylate from tert-butyl (1S,6R,7R)-3bromomethyl-1-oxo-phenylacetamido-3-cephem-4-carboxylate To a stirred mixture of 20.0 g (purity 90%, 37.2 mmoles) of tert-butyl (1S,6R,7R)-3-bromomethyl-1-oxo-7-phenylacetamido-3-cephem-4-carboxylate (containing 7.5% of the corresponding 7phenylbromoacetamido cephem compound), 42 g of ammonium chloride, 450 ml of dimethylformamide and 90 ml of water 62.5 (0.96 mmoles) of activated zinc powder was added under nitrogen at −6° C. was added. After filtration and washing the residue with 300 ml of ethyl acetate and 100 ml of water, the organic layer was washed with 400 ml of a 0.5 N hydrochloric acid solution and twice with 200 ml of a sodium chloride solution (10%), respectively. The water layers were extracted with 2×250 ml of ethyl acetate. After drying with magnesium sulphate the combined ethyl acetate layers were concentrated until a thick pasta was formed. n-Hexane was added slowly, the mixture was concentrated again, kept at 3° C. for 2 hours and filtered.

After washing the precipitate with n-hexane and drying in vacuo 15.75 g of tert-butyl (1S,4R,6R,7R)-3-methylene-1-oxo-7-phenylacetamidocepham-4-carboxylate was obtained. From the mother liquor another 0.36 mg was obtained. According to a quantitative HPLC-assay the product contained 92.2% of the title compound and 6% of the corresponding deacetoxy compound. The actual yield of the title compound was 92%, taking into account that also the phenylbromoacetamido compound was converted into the title compound.

Example 33

Preparation of tert-butyl (1S,4R,6R,7R)-3-methylene-1-oxo-phenylacetamidocepham-4-carboxylate from tert-butyl (1S,6R,7R)-3-bromomethyl-1-oxo-7-phenylacetamido-3-cephem-4-carboxylate To 250 g (purity 88%, 490 mmoles, containing 8% of the corresponding α-bromophenylacetamido compound) of tert-butyl (1S,6R,7R)-3-bromomethyl-1-oxophenylacetamido-3-cephem-4-carboxylate in 2.5 l of acetone at −17° C. a solution of 200 g ammonium chloride in 450 ml of water and 100 ml of 8 N ammonia was added under nitrogen. Then while maintaining the reaction temperature at −5° C. 250 g (3820 mmoles) of activated zinc powder was added and stirring was continued for 30 minutes. After raising the temperature to 25° C. 500 ml of water and 435 ml of a 4 N hydrochloric acid were added, the reaction mixture was filtered and the residue was washed thoroughly with a mixture of acetone and water (v/v=3:1). To the filtrate (total amount 5100 ml) 4000 ml of water with a temperature of 60° C. was added and the mixture was cooled down and stored for 16 hours at 2° C. The precipitate was filtered off, washed with a mixture of water and acetone (2×250 ml; v/v=3:1) and dried in vacuo at 45° C., giving 174.68 g of the title compound with a purity of 97%. The yield was 85.4%.

IR-spectrum (KBr-disc; values in cm$^{-1}$): 3330, 2980, 1762, 1713, 1646, 1512, 1368, 1340, 1250, 1208, 1153, 1038, 931, 873, 800, 729 and 699.

PMR-spectrum (360 MHz; CDCl$_3$ with some DMSO-d$_6$; tetramethylsilane as an internal reference): δ-values in ppm): 1.45 (s, 9H); 3.59 (s, 2H); 3.61 and 3.73 (ABq, 2H; J=J=14 Hz); 4.91 (d, 1H; J=4.3 Hz); 5.02, 5.37 and 5.64 (singlets, 3H); 5.86 (dd, 1H; J=4.3 and 9.8 Hz); 7.26 (d, 1H; J=9.8 Hz); 7.26 (m, 5H).

Example 34

Preparation of tert-butyl (1S,4R,6R,7R)-3-methylene-1-oxo-7-phenylacetamidocepham-4-carboxylate from tert-butyl (1S,6R,7R)-3-bromomethyl-1-oxo-7-phenylacetamido-3-cephem-4-carboxylate To 100 g (purity 88%, 107 mmoles, containing 8% of the corresponding α-bromophenylacetamido compound) of tert-butyl (1S,6R,7R)-3-bromomethyl-1-oxo-7-phenylacetamido-3-cephem-4-carboxylate in 1 l of dimethyl formamide at −3° C. a warm (45° C.) solution of 80 g ammonium chloride in 180 ml of water was added. Then, while maintaining the reaction temperature at −5° to −10° C., 100 g of activated zinc powder was added and stirring was continued for 60 minutes. After addition of 500 ml of ethyl acetate and 150 ml of water the residue was filtered off and washed with 100 ml of water and 250 ml of ethyl acetate. The layers of the filtrate were separated and the organic layer washed with 400 ml of ethyl acetate, washed with brine (3×100 ml), dried with magnesium sulfate and concentrated while petroleum ether 40°-60° C. was added gradually. After standing overnight the white crystalline precipitate was filtered off, washed with petroleum ether 40°-60° C., and dried in vacuo at 40° C. giving 68.06 g of the title product. Yield 86%.

Example 35

Preparation of 2-bromoethyl (1S,4R,6R,7R)-7-phenylacetamido-3-methylene-1-oxocepham-4-carboxylate from 2-bromoethyl (6R,7R)-3-bromomethyl-1-oxo-7-phenylacetamido-3-cephem-4-carboxylate To 135 g (purity 79%, 199 μmoles) of 2-bromomethyl (6R,7R)-3-bromomethyl-1-oxo-7-phenylacetamido-3cephem-4-carboxylate was added a solution and next 100 mg (1.87 mmole) of ammonium chloride in 0.18 ml of water and 0.10 ml of a 4 N ammonium hydroxide solution and next 125 mg (1.91 mmole) of activated zinc powder. After stirring in an ultrasonic bath at 5° C. for 45 minutes 0.3 ml of a 4 N hydrochloric acid solution was added. The reaction mixture was filtered and the temperature was raised till a clear solution was obtained. Precipitation with 3.5 ml of water gave 63.4 g (61%) of the title product.

IR-spectrum (KBr-disc; values in cm$^{-1}$): 3335, 2975, 1776, 1736, 1652, 1530, 1379, 1342, 1200, 1161, 1031, 942, 868, 729, 697 and 580.

PMR-spectrum (360 MHz; CDCl$_3$; tetramethylsilane as an internal reference): δ-values in ppm): 3.53 (t, 2H; J=5.5 Hz); 3.58 and 3.63 (ABq, 2H; J=15.5 Hz); 3.61 and 3.72 (ABq, 2H; J=14.6 Hz); 4.47 (t, 2H; J=5.5 Hz); 4.87 (d, 1H; J=4.4 Hz); 5.22, 5.43 and 5.73 (3xs, 3H); 5.96 (dd, 1H; J=4.4 and 10.1 Hz); 6.96 (d, 1H; J=10.1 Hz); 7.3 (m, 5H).

Example 36

Preparation of 4-methoxybenzyl (1S,4R,6R,7R)-3-methylene-1oxo-7-phenylacetamidocepham-4-carboxylate from p-methoxybenzyl (1S,6R,7R)-3-bromomethyl-1-oxo-7-phenylacetamido-3-cephem-4-carboxylate To a solution of 40 mg (0.75 mmoles) of ammonium chloride, 70 μl of water and 40 μl of a 4N ammonium hydroxide solution were added 1.0 ml of acetone and 50 mg of activated zinc powder. Then 50 mg (purity 81%, 74 μmoles) of 4-methoxybenzyl (1S,6R,7R)-3-bromomethyl-1-oxo-7-phenylacetamido-3-cephem-4-carboxylate were added and the mixture was stirred in an ultrasonic bath at 0° C. for 1.5 hours. After addition of 0.1 ml of water and 75 μl of a 4 N HCl solution, the mixture was filtered. To the filtrate 1.5 ml of water was added and the crystals formed were filtered off. After washing and drying 36.7 mg of the title compound were obtained with a purity of 76%. Yield 81%.

IR-spectrum (KBr-disc; values in cm$^{-1}$): 3335, 2970, 1775, 1738, 1648, 1611, 1518, 1341, 1257, 1196, 988, 952, 938, 860, 820, 726 and 693.

PMR-spectrum (360 MHz; CDCl$_3$; tetramethylsilane as an internal reference): δ-values in ppm): 3.49 and 3.65 (ABq, 2H; J=14.2 Hz); 3.56 and 3.62 (ABq, 2H; J=15.0 Hz); 3.81 (s, 3H); 4.80 (d, 1H; J=4.4 Hz); 5.07 and 5.13 (ABq, 2H; J=11.9 Hz); 5.16, 5.37 and 5.67 (3xs, 3H); 6.89 (d, 2H; J=8Hz); 7.3 (m, 8H).

Example 37

Preparation of dichloroethyl (1S,4R,6R,7R)-7-phenylacetamido-3-methylene-1-oxocepham-4-carboxylate and (1S,4R,6R,7R)-7-phenylacetamido-3-methylene-1oxocephem-4-carboxylic acid from trichloroethyl (6R,7R)-3-bromomethyl-1-oxo-7-phenylacetamido-3-cephem-4-carboxylate 1.2 g (22.4 mmoles) of ammonium chloride in 2.2 ml of water and 1.2 ml of a 4 N hydroxide solution at −10° C. were added to a stirred solution of 1.68 g (purity 92%; 2.78 mmoles) of trichloroethyl (1S,4R,6R,7R)-3-bromomethyl-1-oxo-7-phenylacetamidocephem-4-carboxylate in 15 ml of acetone and 2 ml of dimethylformamide. After adding 1.5 g (15.3 mmoles) of activated zinc powder the mixture was stirred at 4° C. for 70 min. Then 3 ml of water and 3.6 ml of a 4 N hydrochloric acid solution were added and the solid material was filtered off. To the filtrate 50 ml of warm water was added. After cooling to 0° C. the crystals were filtered off, washed and dried giving 153 mg of dichloro-ethyl (1S,4R,6R,7R)-7-phenylacetamido-3-methylene-1-oxocepham-4-carboxylate with a purity of 83%. Yield 10%.

IR-spectrum (KBr-disc; values in cm$^{-1}$): 3300, 2930, 2850, 1780, 1750, 1649, 1574, 1521, 1377, 1351, 1340, 1182, 1155, 1026, 940, 864, 758, 727, 692, 665, 581 and 528.

PMR-spectrum (360 MHz; CDCl$_3$ and some DMSO-d$_6$; tetramethylsilane as an internal reference): δ-values in ppm): 3.58 and 3.73 (ABq, 2H; J=14.4 Hz); 3.59 and 3.63 (ABq, 2H; J=15.2 Hz); 4.53 (m, 2H); 4.84 (d, 1H; J=4.4 Hz); 5.26, 5.45 and 5.75 (3xs, 3H); 5.86 (t, 1H; J=5.7 Hz); 5.98 (dd, 1H; J=4.4 and 10.2 Hz); 6.91 (d, 1H; J=10.2 Hz); 7.3 (m, 5H).

The mother liquor was extracted several times with methylene chloride. The methylene chloride solution was concentrated and triturated with ether giving 769 mg of (1S,4R,6R,7R)-7-phenyl-acetamido-3-methylene-1-oxocepham-4 -carboxylic acid. Purity 87%; yield 69%. Total yield 79%.

Example 38

Preparation of tert-butyl (1S,4R,6R,7R)-3-methylene-1-oxo-7-phenylacetamidocepham-4-carboxylate from tert-butyl (6R,7R)-3bromomethyl-7-[(2-bromo-2-phenyl)acetamido]-1-oxo-3-cephem-4-carboxylate To a solution of 10 g (17.78 mmoles) of tert-butyl (1S,6R,7R)-3-bromomethyl-7-[(2-bromo-2-phenyl)acetamido]-1oxo-3-cephem-4-carboxylate in 125 ml of dimethyl-formamide and 22.5 ml of water, under a nitrogen atmosphere and cooled in an ice bath, were added 10 g of ammonium chloride and 12.5 g of activated zinc powder while the mixture was stirred. After 45 minutes 60 ml of ethyl acetate and 20 ml of water was added and the reaction mixture was filtered. The filtrate was washed with 30 ml of water and 50 ml of ethyl acetate and the layers were separated. After washing a 10% sodium chloride solution (3×50 ml) the ethyl acetate solution was dried (magnesium sulphate) and concentrated. Some n-hexane and ethyl acetate was added and the solution was again concentrated to a small volume. The precipitate was filtered and washed with n-hexane and dried in vacuo yielding 6.75 g (94%) of the white crystalline title compound.

Example 39

Preparation of diphenylmethyl (1S,4R,6R,7R)-7formamido-3-methylene-1-oxocepham-4-carboxylate from diphenylmethyl (1S,6R,7R)-3bromomethyl-7-formamido]-1oxo-3-cephem-4-carboxylate To a chilled solution of 3 g (purity 74%; 4.40 mmoles) of diphneylmethyl (1S,6R,7R)-3-bromomethyl-7-formamido-1-oxo-3-cephem-4-carboxylate in 25 ml of dimethylformamide was added at −15° C. a solution of 2.4 g (4.49 mmoles) of ammonium chloride, 4.2 ml of water and 2.4 ml of a 4N sodium hydroxide solution. After adding 3 g (30.6 mmoles) of activated zinc powder at 0° C. the reaction mixture was stirred for 35 min. while the temperature was kept at 0° C. After adjusting the pH of the reaction mixture to 2 with 7 ml of a 4 N hydrochloric acid solution, the inorganic residue was filtered off and washed with 25 ml of dimethylformamide. Addition of 75 ml of water to the filtrate gave white crystals after standing overnight (2.05 g; purity 86%); yield 94.5%).

IR-spectrum (KBr-disc; values in cm$^-$); 3360, 2965, 1781, 1733, 1660, 1527, 1458, 1352, 1237, 1198, 1091, 1031, 988, 967, 940, 866, 741 and 701.

PMR-spectrum (360 MHz; CDCl$_3$; tetramethylsilane as an internal reference; δ-values in ppm): 3.44 and 3.69 (ABq, 2 H; J=14.2 Hz); 4.86 (d, 1H; J=4.4 Hz); 5.35, 5.47 and 5.82 (3xs, 3H); 5.99 (dd, 1H; J=4.4 and 10.2 Hz); 6.86 (s, 1H); 7.11 (d, 1H; J=10.2 Hz); 7.3 (m, 10H); 8.23 (s, 1H).

Example 40

Preparation of (4R,6R,7R)-7-amino-3-methylenecepham-4-carboxylic acid from (6R,7R)-3-bromomethyl-4-carboxy-7-isopropylideneammonio-3-cephem bromide To a stirred mixture of 7.79 g (purity 80.7%; 15.18 mmoles) of (6R,7R)-3-bromomethyl-4-carboxy-7-isopropylideneammonio-3-cephem bromide, 4 g of ammonium chloride, 10 ml of water and 50 ml of N,N-dimethylformamide was added 2.7 g (19,8 mmoles) of activated zinc powder at −2° C. After stirring for 110 minutes at 0° C. and addition of 6.5 ml of a 4 N hydrochloric acid solution (pH is 1.8) the reaction mixture was filtered and the residue was washed with 10 ml of a 1 N hydrochloric acid solution. The pH of the filtrate was adjusted to 4 by adding 6.7 ml of a 4 N sodium hydroxide solution, and the crystals formed were filtered off and washed with 10 ml of water-acetone (1:1) and acetone, respectively, giving after drying 1.8 g of the title compound. Yield 53%.

Example 41

Preparation of 7-amino-3-exomethylenecepham-4-carboxylic acid from 3-bromomethyl-4-carboxy-7β-isopropylideneammonio-3-cephem bromide Under nitrogen atmosphere, 3 g (5.7 mmoles) of 3-bromomethyl-4-carboxy-7β-isopropylideneammonio-3-cephem bromide was added with stirring to a mixture of 4 g ammonium chloride, 10 ml of water, 40 ml of dimethylformamide and 5 g of activated zinc powder. After 30 minutes the pH was adjusted to 1.8 with 3.5 ml of 4 N HCl. After filtration and washing with 10 ml of acetone/water (1:1 v/v), the pH of the solution was adjusted to 3.9. After 30 minutes the precipitate was filtered off, washed with acetone/water and with acetone and dried, giving 0.5 g of the title product.

IR-spectrum (KBr disc, values in cm$^{-1}$): 3430, 2190, 1780, 1630, 1550, 1370, 1220, 1147, 1125, 1010, 938, 855, 800, 766, 704, 655, 420, 400 and 370 cm$^{-1}$.

PMR-spectrum (CF$_3$COOD; δ-values in ppm): 3.24 and 3.55 (2xd, 2H; J=14 Hz); 4.99 (d, 1H; J=4.1 Hz); 5.17, 5.24 and 5.27 (3xs, 3H); 5.48 (d, 1H; J=4.1 Hz).

Example 42

Preparation of tert-butyl (1S,4R,6R,7R)-7-formamido-3-methylene-1-oxocepham-4-carboxylate from tert-butyl (1S,6R,7R)-2-bromo-3-bromomethyl-7-formamido-1-oxo-3-cephem-4-carboxylate To a stirred mixture of 2.0 g (purity 86.3%; 3.66 mmoles) of tert-butyl (1S,6R,7R)-2-bromo-3-bromomethyl-7-formamido-1-oxo-3-cephem-4carboxylate, 1.8 g of ammonium chloride, 4 ml of water and 25 ml of N,N-dimethylformamide was added 1.0 g (15.3 mmoles) of activated zinc powder at −8° C. After stirring for 10 minutes 20 ml of methylene chloride and 5 ml of water was added, the residue was filtered off and washed with methylene chloride (2×15 ml) and water (5 ml). After separation of the layers and extracting the water layer with 20 ml of methylene chloride the combined organic layers were washed with brine, dried with magnesium sulphate and concentrated. Adding slowly an excess of water and cooling for some time in an ice bath the crystalline precipitate was filtered off and dried in vacuo giving 0.83 g of the title compound with a purity of 87.7%. The yield was 63%.

IR-spectrum (KBr disc, values in cm$^{-1}$): 3440, 2992, 1774, 1720, 1658, 1510, 1391, 1370, 1347, 1289, 1238, 1211, 1155, 1094, 1037, 947, 870, 839, 800, 732, 620 and 583.

PMR-spectrum (360 MHz; CDCl$_3$ with some DMSO-d$_6$, δ-values in ppm; tetramethylsilane as an internal reference): 1.47 (s, 9H); 3.74, 3.84 (ABq, 2H; J=14.4 Hz); 5.04, 5.40, 5.65 (3s, 3H); 5.06 (d, 1H; J=4.8 Hz); 5.81 (dd, 1H; J=4.8 and 10.1 Hz); 8.08 (d, 1H; J=10.1 Hz); 8.20 (s, 1H).

Example 43

Preparation of tert-butyl (1S,4R,6R,7R)-3-bromomethylene-7-formamido-1-oxocepham-4-carboxylate from tert-butyl (1S,6R,7R)-3-dibromomethyl-7-formamido-1-oxo-3-cephem-4-carboxylate Activated zinc powder (0.7 g) was added to a mixture of 500 mg of tert-butyl (1S,6R,7R)-3-dibromomethyl-7-formamido-1oxo-3-cepham-4-carboxylate, 7 ml of dimethyl-formamide, 1.25 ml of water and 0.55 g of ammonium chloride at 5° C. and the mixture was stirred for 1 hour at 2° C. Then 4 ml of ethyl acetate and 1 ml of water were added, the mixture was filtered and the residue was washed with 2 ml of water and 3 ml of ethyl acetate. After separating the layers the organic layer was washed with brine, dried with magnesium sulphate and concentrated to about 1 ml. After standing overnight the white precipitate was filtered off, washed with diethylether and dried, giving 240 mg (58%) of the title product.

IR-spectrum (KBr disc, values in cm$^{-1}$): 3330, 2994, 1778, 1723, 1673, 1518, 1371, 1345, 1240, 1155, 104, 960, 874, 768, 738, 731 and 589.

PMR-spectrum (360 MHz; CDCl$_3$; δ-values in ppm): tetramethylsilane as an internal reference); 1.48 (s, 9H); 3.47, 4.54 (ABq, 2H; J=14.4 Hz); 5.00 (d, 1H; J=4.3 Hz); 5.17 (s, 1H); 5.95 (dd, 1H; J=4.3 and 10.4 Hz); 7.08 (s, 1H); 7.55 (d, 1H; J=10.4 Hz); 8.23 (s, 1H).

Example 44

Preparation of tert-butyl (1S,4R,6R,7R)-3-methylene-1,1-dioxo-7-phenylacetamidocepham-4-carboxylate from tert-butyl (6R,7R)-3-bromomethyl-1,1-dioxo-7-phenylacetamido-3-cephem-4-carboxylate To a solution of 40 mg (0.75 mmoles) of ammonium chloride, 70 82 1 of water and 40 μl of a 4 N ammonium hydroxide solution were added 0.5 ml of acetone and 50 mg of activated zinc powder. Then 50 mg (purity 94%; 94 μmoles) of tert-butyl (6R,7R)-3-bromomethyl-1,1-dioxo-7-phenylacetamido-3-cephem-4-carboxylate were added and the mixture was stirred in an ultrasonic bath at 0° C. for 35 minutes. After addition 0.1 ml water, 0.2 ml of a 4 N HCl solution and 0.2 ml of methanol, the mixture was filtered. To the filtrate 1.5 ml of water was added and the crystals formed were filtered off. After washing and drying 34 mg of the title compound was obtained with a purity of 94%. Yield: 81%.

IR-spectrum (KBr-disc; values in cm$^{-1}$): 3400, 2975, 1777, 1741, 1703, 1522, 1372, 1320, 1257, 1150, 1119, 938, 868, 831, 702, 569 and 513.

PMR-spectrum (360 MHz; CDCl$_3$ and some DMSO-d$_6$; tetramethylsilane as an internal reference: δ-values in ppm): 1.47 (s, 9H); 3.63 (s, 2H); 3.76 and 3.91 (ABq; J=14.2 Hz); 4.99, 5.40 and 5.48 (s, 3H); 5.14 (d. 1H; J=4.4 Hz); 6.05 (dd, 1H; J=4.4 and 10.2 Hz); 7.3 (m, 6H).

Example 45

Preparation of tert-butyl (1S,4R,6R,7R)-3-methylene-1-oxo-7-phenylacetamidocepham-4-carboxylate from tert-butyl (1S,6R,7R)-3-bromomethyl-1-oxo-7-phenylacetamido-3-cephem-4-carboxylate To a stirred solution of 480 mg (1 mmole) of tert-butyl (1S,6R,7R)-3-bromomethyl-1-oxo-7-phenylacetamido-3-cephem-4-carboxylate in 12.5 ml of dimethylformamide was added 2.5 ml of water, 1 g of ammonium chloride and 500 mg of magnesium powder at 0° C. After stirring for 2 hours at 0° C. 100 ml of ethyl acetate was added. After filtration the diluted reaction mixture was subsequently washed with water, 1 N hydrochloric acid, brine, and dried with magnesium sulfate. After treating the dried solution with diethylether and n-hexane the title product was filtered off, washed with n-hexane and dried, yielding 382 mg of tert-butyl (1S,4R,6R,7R)-3-methylene-1-oxo-7phenylacetamido-cepham-4-carboxylate The invention now being fully described, it will be apparent to one of ordinary skill in the art that many changes can be made thereto without departing from the spirit or scope of the appended claims.

We claim:

1. A process for the preparation a 3-methylene or 3-halomethylene cepham compound of the formula

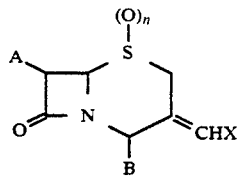

wherein,
A is an amino group or a protected amino group,
B is a carboxy group or a protected carboxy group, or a salt thereof,
X is hydrogen or halogen, and
n is 1 or 2,
comprising reacting a compound of the formula

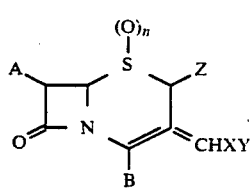

wherein A, B, X and n are defined as above, Y is a halogen and Z is Y or hydrogen with an activated metal in the presence of an ammonium salt or an amine and optionally a base to form the compound of formula I.

2. The process of claim 1 wherein the ammonium salt is ammonium chloride and the base is ammonium hydroxide.

3. The process of claim 1 wherein the activated metal is selected from the group consisting of zinc and magnesium.

4. The process of claim 2 wherein the activated metal is zinc.

* * * * *